US00PP33999P2

(12) United States Plant Patent
Smith

(10) Patent No.: US PP33,999 P2
(45) Date of Patent: Mar. 8, 2022

(54) ***CHRYSANTHEMUM* PLANT NAMED 'CIFZ0083'**

(50) Latin Name: ***Chrysanthemum* x *morifolium***
Varietal Denomination: CIFZ0083

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/233,662

(22) Filed: Apr. 19, 2021

(51) Int. Cl.
*A01H 5/02* (2018.01)
*A01H 6/14* (2018.01)

(52) U.S. Cl.
USPC ..... Plt./288

(58) Field of Classification Search
USPC ..... Plt./287, 288, 289
CPC ... A01H 5/02; A01H 5/00; A01H 6/14; A01H 6/1424
See application file for complete search history.

(56) References Cited

U.S. PATENT DOCUMENTS

PP30,154 P2 * 1/2019 Heimovaara ..... A01H 5/02 Plt./294
PP31,045 P2 * 11/2019 Smith ..... A01H 6/1424 Plt./287

OTHER PUBLICATIONS

Daily Journal 5 answers about mums 2016, retrieved on Jun. 24, 2021, retrieved from the Internet at https://www.daily-journal.com/life/home_garden/5-answers-about-mums/article_8314ee16-a316-50cf-a4d3-288893b58fea.html, 3 pp. (Year: 2016).*

* cited by examiner

*Primary Examiner* — June Hwu
(74) *Attorney, Agent, or Firm* — Dale Skalla

(57) ABSTRACT

A new garden type *Chrysanthemum* plant named 'CIFZ0083' particularly distinguished by its medium large size plant with mound plant habit, a small size decorative flower, white flower color with pinkish tips, under cool temperatures having a yellow center in young flowers, and a natural season response early October.

1 Drawing Sheet

Figure 1:
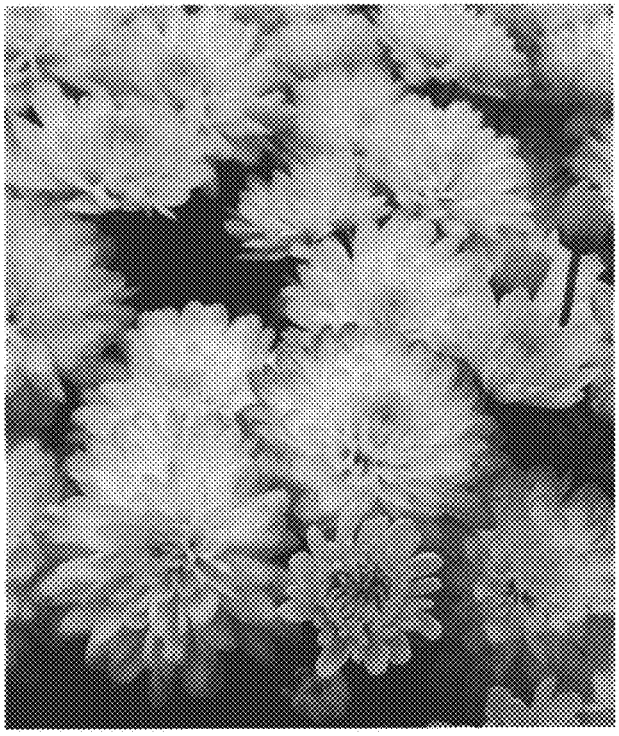

Latin name of the genus and species of the plant claimed: *Chrysanthemum* x *morifolium*.

Varietal denomination: 'CIFZ0083'.

BACKGROUND OF THE NEW PLANT

The present invention comprises a new *Chrysanthemum*, botanically known as *Chrysanthemum* x *morifolium*, and hereinafter referred to by the variety name 'CIFZ0083'.

'CIFZ0083' is a product of a planned breeding program. The new cultivar has medium large size plant with mound plant habit, a small size decorative flower, white flower color with pinkish tips, under warmer temperatures will start creamy, become white, and have little to none of the pinking as they age, and a natural season response early October.

'CIFZ0083' originated from a mutation of X-ray treated cuttings in October 2015 in Gilroy, Calif. 'CIFZ0083' was selected from the resulting plants on Mar. 8, 2016 in Gilroy, Calif.

The female parent was an unnamed sport from 'Nikki Pink Bicolor', '10-M078IB'.

TABLE 1

Characteristics of the female parent, compared to 'CIFZ0083':

| Trait | 'CIFZ0083' | '10-M078IB' |
|---|---|---|
| Natural response: | 1 week slower | 1 week faster |
| Blackcloth response: | Similar | Similar |

TABLE 1-continued

Characteristics of the female parent, compared to 'CIFZ0083':

| Trait | 'CIFZ0083' | '10-M078IB' |
|---|---|---|
| Flower size: | Similar | Similar |
| Flower color: | Whiter | Pinker |
| Flower type: | Similar | Similar |
| Plant size: | Similar | Similar |
| Plant habit: | Similar | Similar |

As the new variety is the result of mutation breeding, there is not a male parent. The first act of asexual reproduction of 'CIFZ0083' was accomplished when vegetative stem cuttings were propagated from the initial selection in May 2016 in Gilroy, Calif.

BRIEF SUMMARY OF INVENTION

Horticultural examination of plants grown from cuttings of the plant initiated in May 2016 and continuing thereafter, has demonstrated that the combination of characteristics as herein disclosed for 'CIFZ0083' are firmly fixed and are retained through successive generations of asexual reproduction.

'CIFZ0083' has not been observed under all possible environmental conditions. The phenotype may vary significantly with variations in environment such as temperature, light intensity and day length.

A Plant Breeder's Right for this cultivar has not yet been applied for. 'CIFZ0083' has not been made publicly available prior to the effective filing date of this application, notwithstanding any disclosure that may have been made less than one year prior to the effective filing date of this application by the inventor or another who obtained 'CIFZ0083' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0083' with colors being as true as possible with an illustration of this type.

Figure 2:
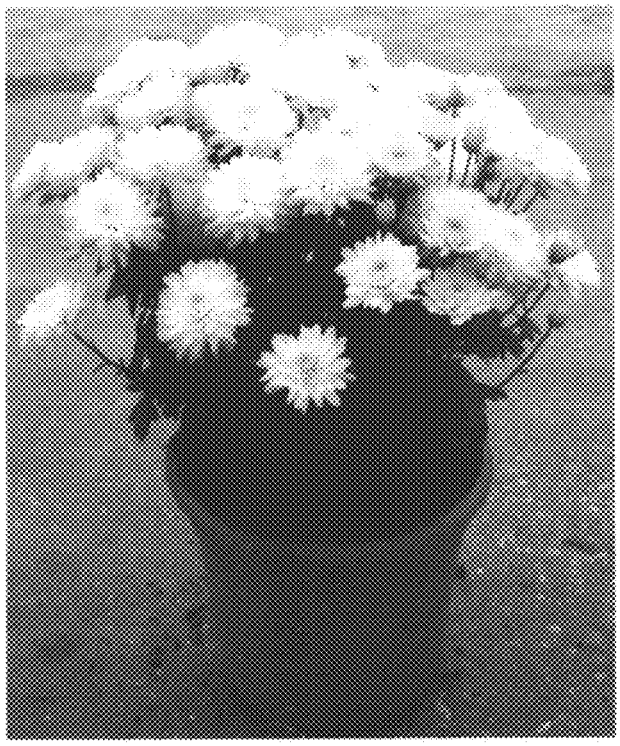

The photographic drawing shows in FIG. 1 a close view of flower of the new variety and in FIG. 2 a flowering plant from an indoor trial.

The aforementioned photographs: FIG. 1, as well as FIG. 2 were taken in March 2021 both showing a plant from the same blackcloth indoor trial in Enkhuizen, The Netherlands.

These plants were about 10 weeks of age. One rooted cutting per pot had been planted in a one gallon pot, not pinched in week 53, 2020 and black clothed from week 3. Plants started flowering mid March 2021.

DETAILED BOTANICAL DESCRIPTION

The measurements were taken in Gilroy, Calif. in September 2020 on the plants from an indoor blackcloth trial in Gilroy, Calif.

Color references are made to The Royal Horticultural Society Colour Chart (R.H.S.) 2015.

TABLE 2

DIFFERENCES BETWEEN THE NEW VARIETY 'CIFZ0083' AND TWO MOST SIMILAR VARIETIES:

| Trait | 'CIFZ0083' | 'CIFZ0063', U.S. Plant Pat. No. 31,045 |
|---|---|---|
| Natural response: | ½ week slower | ½ week faster |
| Blackcloth response: | Similar | Similar |
| Mature flower diameter: | 3.5 cm | 4.4-4.7 cm |
| Flower color: | White | Pink/lavender with white bicolor center |
| Flower type: | Similar | Similar |
| Plant size: | Bit smaller | Bit larger |
| Plant habit: | Similar | Similar |
| Flower longevity: | Longer lasting/ less color fade | Shorter lasting/more color fade |

TABLE 3

| Trait | 'CIFZ0083' | 'Zanmulpine', U.S. Plant Pat. No. 30,154 |
|---|---|---|
| Natural response: | ½ week slower | ½ week faster |
| Blackcloth response: | ½ week slower | ½ week faster |
| Flower size: | Bit smaller | Bit larger |
| Flower color: | Creamier white | Whiter white |
| Flower type: | Similar | Similar |
| Plant size: | 19-21 cm in height; 30 cm width | 35-45 cm in height; 60-70 in diameter |
| Plant habit: | Similar | Similar |

Plant:

*Form, growth and habit.*—Herbaceous garden-type, stems Upright and outwardly spreading, freely branching, strong and moderately vigorous growth habit.

*Plant height (above soil).*—17-19 cm.

*Plant height (inflorescence included).*—19-21 cm.

*Plant width.*—30 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B but whiter.

Foliage:

*Arrangement.*—Alternate.

*Immature leaf, color upper surface.*—RHS NN137A.

*Immature leaf, color lower surface.*—RHS 137C.

*Mature leaf, color, upper surface.*—RHS NN137A.

*Mature leaf, color lower surface.*—RHS NN137C.

*Length.*—3.0 cm.

*Width.*—2.0 cm.

*Shape.*—Ovate, with distinct lobes.

*Base shape.*—Attenuate.

*Apex shape.*—Mucronate.

*Margin.*—5-lobed (palmate), edge dentate.

*Number of margin indentations.*—Medium.

*Depth of margin indentations.*—Shallow.

*Leaf length terminal lobe relative to total leaf length.*—Short.

*Leaf depth lower lateral sinus.*—Shallow.

*Texture, upper surface.*—Bifid hairs.

*Texture, lower surface.*—Bifid hairs.

*Color of veins, upper surface.*—RHS 138B.

*Color of veins, lower surface.*—RHS 138A.

*Pattern of veining.*—Palmate.

*Petiole color.*—RHS 137A.

*Petiole Length.*—1.0-1.1 cm.

*Diameter.*—0.2-0.3 cm.

*Texture.*—Bifid hairs.

*Presence of stipules.*—Yes.

*If present, size of stipules.*—Small.

Stem:

*Quantity of main branches per plant.*—6-8.

*Color of stem.*—RHS 138A.

*Length of stem.*—8.0 cm.

*Diameter.*—0.5 cm.

*Length of internodes.*—2.0-2.5 cm.

*Texture.*—Bifid hairs.

*Color of peduncle.*—RHS 138A.

*Length of peduncle.*—3.0-3.5 cm.

*Peduncle diameter.*—0.2-0.3 cm.

*Texture.*—Bifid hairs.

Inflorescence:

*Type.*—Compositae, solitary, decorative-type inflorescences borne terminally above foliage, ligulate ray florets arranged acropetally on a capitulum giving a double flower.

*Quantity of short days to flowering (response time).*—Approximately 7.5 weeks.

*Quantity of inflorescences per plant.*—80-120 with many small buds developing.

*Lastingness of individual blooms on the plant.*—About six weeks from first color.

*Fragrance.*—Slightly spicy.

Bud (when showing color):
*Color*.—RHS 1C.
*Length*.—0.8-0.9 cm.
*Width*.—0.8-0.9 cm.
*Shape*.—Oblate.
Immature inflorescence (at moment of opening):
*Diameter*.—2.0-2.5 cm.
*Color of ray florets, upper surface*.—RHS 8B; darkest at apex.
*Color of ray florets, lower surface*.—RHS 8D.
Mature inflorescence:
*Diameter*.—3.5 cm.
*Depth*.—1.2 cm.
*Total diameter of disc*.—No disc present.
*Receptacle color*.—RHS 143C.
*Receptacle height*.—0.5 cm.
*Receptacle diameter*.—1.0 cm.
*Length of corolla tube*.—Short.
Ray florets:
*Average quantity of florets*.—140-150 in several whorls.
*Color of florets, upper surface*.—RHS NN155B with RHS N66C at the tips.
*Color lower surface*.—RHS NN155B.
*Length*.—1.7 cm.
*Width/diameter*.—0.6 cm.
*Longitudinal axis curvature strength of the inner and outer rows*.—Weak.
*Shape*.—Elliptical.
*Apex shape*.—Mostly obtuse and dentate.
*Base shape*.—Tube.
*Margin*.—Entire Small incisions may be present at tip.
*Margin*.—type of rolling Weakly involute.
*Texture, upper surface*.—Papillate.
*Lower surface*.—Papillate.
*Ribs present*.—Yes.
*Number of keels*.—2.
*Profile at widest point*.—Moderately convex.
*Longitudinal axis shape*.—Reflexing.
Disc florets:
*Number of disc florets*.—0.
Inflorescence (at moment of senescence):
*Color of ray florets, upper surface*.—RHS NN155B with RHS N66C at tips.
*Color of ray florets, lower surface*.—RHS NN155C with RHS N66C at tips.
Phyllaries:
*Quantity*.—20-25.
*Color, upper surface*.—RHS 143C.
*Color, lower surface*.—RHS 143A.
*Length*.—0.6 cm.
*Width*.—0.1-0.2 cm.
*Shape*.—Lanceolate.
*Apex shape*.—Acute.
*Base*.—Fused.
*Margins*.—Entire.
*Texture, upper surface*.—Glabrous.
*Texture, lower surface*.—Canescent.
Reproductive organs:
*Pistil*.—One.
*Length*.—0.4 cm.
*Style color*.—RHS 150C.
*Style length*.—0.3 cm.
*Stigma color*.—RHS 144A.
*Stigma shape*.—Bi-parted.
*Ovary color*.—RHS 145C.
*Ovary length*.—0.2 cm.
*Ovary width*.—0.1 cm.
Androecium: As no disc florets developed in the flower, no androecium was present.
*Fertility/seed set*.—Has not been determined to date.
*Disease/pest resistance*.—Has not been determined to date.
*Hardiness*.—Has not been determined to date.

What is claimed is:

1. A new and distinct variety of *Chrysanthemum* plant named 'CIFZ0083' substantially as illustrated and described herein.

* * * * *